(12) United States Patent
Abela

(10) Patent No.: US 6,389,307 B1
(45) Date of Patent: May 14, 2002

(54) FLUORESCENCE SENSING OF TISSUE

(76) Inventor: George S. Abela, 6201 Windrush La., E. Lansing, MI (US) 48823

( * ) Notice: Subject to any disclaimer, the term of this patent is extended or adjusted under 35 U.S.C. 154(b) by 0 days.

(21) Appl. No.: 09/285,719

(22) Filed: Apr. 5, 1999

(51) Int. Cl.[7] ............................................. A61B 6/00
(52) U.S. Cl. .................................................... 600/478
(58) Field of Search ................................ 600/310, 407, 600/409, 410, 417, 424, 425, 429, 434, 437, 473, 478, 475, 476, 479, 483; 604/19, 20, 21, 22, 94, 96, 97, 98; 606/2, 7, 13, 14, 15, 16

(56) References Cited

U.S. PATENT DOCUMENTS

| | | | |
|---|---|---|---|
| 4,785,806 A | * 11/1988 | Deckelbaum | 128/303.1 |
| 4,860,743 A | 8/1989 | Abela | |
| 5,061,265 A | 10/1991 | Abela et al. | |
| 5,293,872 A | * 3/1994 | Alfano et al. | 128/664 |
| 5,646,404 A | 7/1997 | Litzkow et al. | |
| 5,651,785 A | * 7/1997 | Abela et al. | 606/8 |

* cited by examiner

Primary Examiner—Marvin M. Lateef
Assistant Examiner—Jeoyuh Lin
(74) Attorney, Agent, or Firm—Miles & Stockbridge P.C.

(57) ABSTRACT

Tissue of a patient is tested for dangerous characteristics by using a laser that stimulates fluorescence in the tissue. The laser energy is applied to the tissue by from an opening in a catheter, which catheter supplies clear flushing solution out the same opening. The clear solution therefore provides a clear path for the laser energy and for the fluorescent light from the tissue. An optical fiber carries the laser energy to a distal end of the catheter and carries back fluorescent light to a proximal end of the catheter. The fluorescent light is checked for fluorescent peaks by a detection subsystem by the proximal end. The detection subsystem may include an optical channel analyzer (OMA). The distal end of the catheter has a dual hood design to best provide for the passage of light and clear flushing solution through the same opening. A balloon is used in some embodiments to maintain the clear path for the light for a longer time period than otherwise possible or appropriate.

23 Claims, 2 Drawing Sheets

FLUORESCENCE SENSING OF TISSUE

BACKGROUND OF THE INVENTION

The present invention relates to sensing of tissue characteristics in vivo in a patient (human or non-human animal). More specifically, the present invention relates to detection of fluorescence characteristics of tissue for diagnosis and definition (i.e., distinguishing tissues of different types) purposes.

Various medical diagnostic and treatment techniques involve detection of tissue characteristics. For example, checking for fluorescence of tissue has been used for early detection of cancer in the esophagus and other parts of the gastrointestinal tract. Also, such fluorescence has been used to detect plaque in arterial walls. The amplitude, steepness, and spectral location of peaks in the fluorescence (i.e., wavelengths of greatest amount of light) are indicative of the characteristics of the plaque including the thickness of its collagen which supports the fat in the plaque. However, the resolution in such fluorescence techniques has been less than desirable at least in some circumstances where plaque characteristics are important.

Finding the plaque which is most prone to rupture or thrombosis is difficult. That kind of plaque poses the most immediate danger to a patient. Therefore, early detection of certain subtle characteristics of that most dangerous kind of plaque is important. Many plaque detection techniques do not provide sufficient resolution for early detection of the dangerous plaque.

Among various other tissue detection techniques, use of magnetic resonance imaging (MRI) may allow the detection of plaque in arteries.

Another technique used for tissue characteristic sensing is ultrasound. This is useful in some circumstances, but lacks sufficient resolution for other circumstances such as reliable early detection of dangerous plaque.

Infrared (IR) detection of tissue provides information about the tissue characteristics. However, this technique again lacks sufficient resolution for other circumstances such as reliable early detection of dangerous plaque.

Angioscopic imaging of tissue can provide information about condition of arterial tissues. However, this technique involves colorimetry and software that infers the characteristics of plaque indirectly. The indirect inference makes this of questionable accuracy under at least some circumstances.

U.S. Pat. No. 5,061,265, co-invented by the present inventor, issued Oct. 29, 1991, and hereby incorporated by reference, disclosed laser ablation of cardiovascular tissue, such as plaque on arterial walls, by use of a double hood catheter. That technique used a power laser beam exiting an inner hood, passing through a clear fluid between the inner hood and an outer hood, and passing out of an opening in the outer hood. The clear fluid passed out the opening and it, together with the structure of the catheter, prevented build up of burned blood cells or other materials on the inner hood. In that fashion, a high power laser beam was able to apply sufficient power to ablate plaque.

U.S. Pat. No. 4,860,743, entitled "LASER METHOD AND APPARATUS FOR THE RECANALIZATION OF VESSELS AND TREATMENT OF OTHER CORONARY CONDITIONS" issued Aug. 29, 1989 in the name of Dr. George S. Abela, the present inventor, is also incorporated by reference. That patent disclosed some underlying techniques of laser ablation, which techniques were modified and improved in the above referenced '265 patent.

OBJECTS AND SUMMARY OF THE INVENTION

Accordingly, it is a primary object of the present invention to provide a new and improved imaging system and method.

A more specific object of the present invention is to provide improved fluorescence detection of tissues.

A further object of the present invention is to provide improved resolution in detection of characteristics of cardiovascular tissue such as plaque on arterial walls.

Yet another object of the present invention is to provide a catheter technique where fluorescence detection is improved by providing a clear fluid for the light to pass through.

The above and other features of the present invention which will be more readily understood when the following detailed description is considered in conjunction with the accompanying drawings are realized by a system for medical diagnosis including: a catheter with a proximal end and a distal end and having: an outer hood having a first opening disposed therein; an optical fiber having a tip within the outer hood, the optical fiber operable to output a diagnostic laser beam with a central axis extending from the tip through the first opening; and a channel connected to the outer hood and extending along the catheter for supplying flushing solution to within the outer hood such that the flushing solution flows out of the first opening. A detection subsystem is operably connected to the proximal end of the catheter and operable to detect fluorescent light from tissue illuminated by the diagnostic laser beam, the fluorescent light having passed from the distal end of the catheter to the proximal end of the catheter along the optical fiber.

The present invention may alternately be described as a method of medical diagnosis, the steps including: inserting a distal end of a catheter into a patient, the catheter also having a proximal end and including an outer hood having a first opening disposed therein; outputting a diagnostic laser beam from within the outer hood to pass through the opening and be applied to tissue of the patient; sensing fluorescent light from the laser stimulation of the tissue; and supplying clear solution to the opening such that the diagnostic laser beam and the fluorescent light have relatively clear paths.

BRIEF DESCRIPTION OF THE DRAWINGS

The above and other features of the present invention will be more readily understood when the following detailed description is considered in conjunction with the accompanying drawings wherein like characters represent like parts throughout the several views and in which.

DETAILED DESCRIPTION

Figure 1:
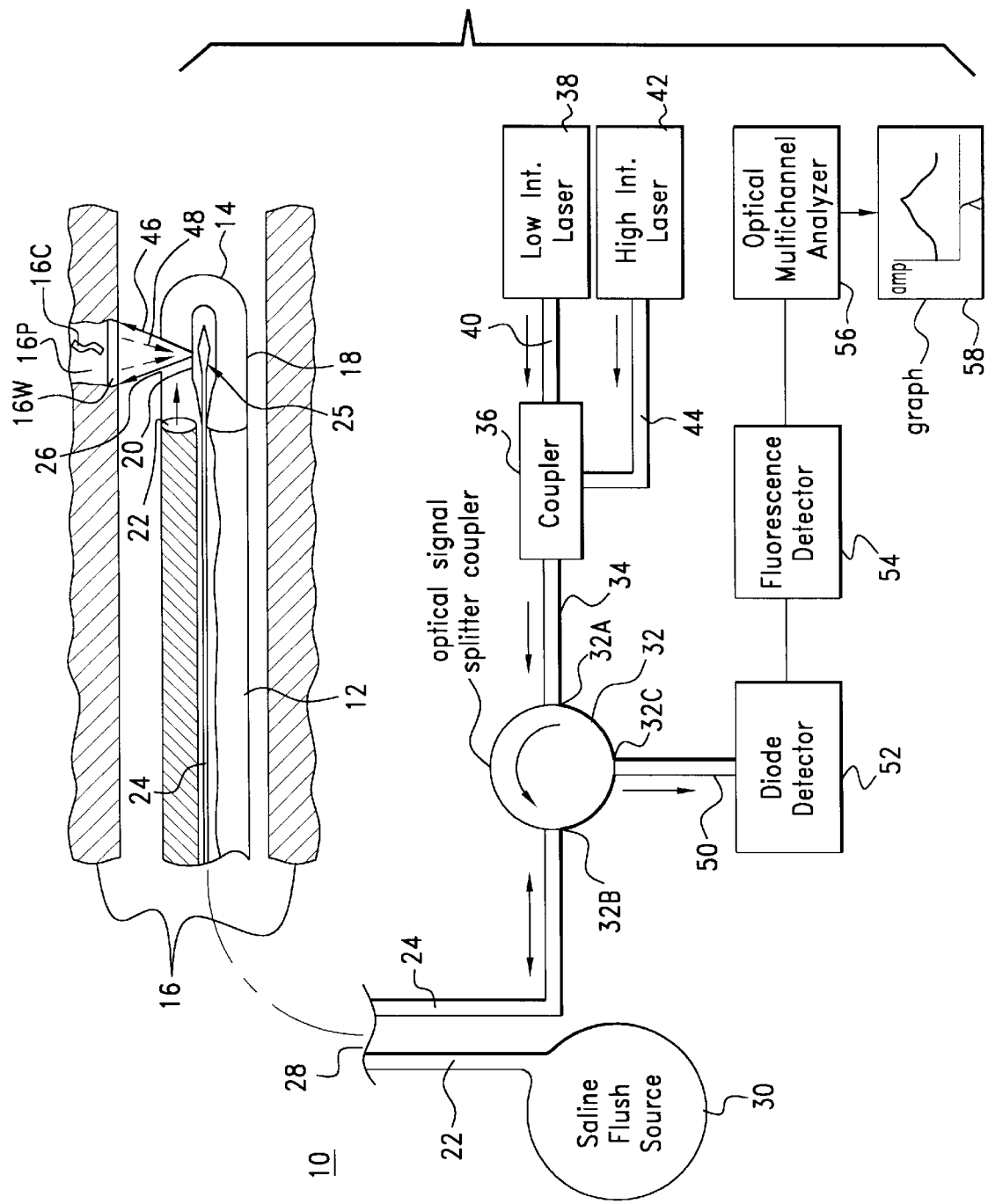
FIG. 1 is a simplified side view with portions in cross section of a distal end of a catheter combined with a simplified block diagram of components connected to the catheter.

Turning now to FIG. 1, the system 10 used for a first embodiment of the present invention is shown. The system includes a catheter 12 having a distal end 14, which is shown within arterial wall tissue 16 that is part of a patient.

The catheter 12 has a design as disclosed in the incorporated by reference '265 patent. An outer hood 18, an inner hood 20, a flushing solution channel 22, and an optical fiber 24 are constructed and function as described in the '265 patent except as detailed below. Basically, saline or other flushing solution in channel 22 exits the catheter 12 through an opening 26 with laser energy from the fiber 24 going out from the inner hood 20 through opening 26 in the outer hood 18.

The purpose of the laser energy exiting the catheter is different in the present system than that of the '265 patent. As will be discussed in more detail later, the present invention involves the application of laser energy to stimulate fluorescence in tissue for diagnostic purposes.

The proximal end (i.e., portion outside the patient) 28 of catheter 12 is shown in simplified form with the proximal portion of flushing solution channel 22 connected to a source 30 of saline or other flushing solution. The proximal end of optical fiber 24 is connected to a coupler/splitter 32. Coupler/splitter 32 is shown as a circulator where the optical signal entering port 32A goes to port 32B and the optical signal entering port 32B goes to port 32C.

Optical fiber 34 supplies laser energy to port 32A via another coupler 36 which allows low intensity laser 38 to apply laser energy to fiber 40. Therefore, low intensity laser energy from laser 38 passes through fiber 40, coupler 36, fiber 34, coupler/splitter 32, and fiber 24. The laser 38 is preferably a wavelength of 514 nanometers (nm) or less such as 488 nm. When such wavelengths are applied to tissue 16, they stimulate fluorescence that can be collected in the visible range, i.e., 550 to 600 nm. The amplitude, steepness, and spectral location of peaks in the fluorescence (i.e., wavelengths of greatest amount of light) are indicative of the characteristics of the plaque including the thickness of its collagen which supports the fat in the plaque. Generally, the thinner the collagen for a given amount of fat, the more dangerous the plaque is.

The coupler 36 is optional and provides the capability for an optional high intensity laser 42 to apply coagulation energy (i.e., energy to stabilize or solidify the plaque through coagulation of the protein or cross linking the collagen) to tissue 16. This coagulation energy is applied to tissue 16 via fiber 44, coupler 36, fiber 34, coupler/splitter 32, and fiber 24. This provides the ability to treat tissue with the same catheter that is used for diagnosis. Specifically, the tissue 16, as shown schematically on a portion thereof, has a cap 16W (at the wall of the artery) with a lipid pool (fat) 16P and collagen 16C there below. The dangerous plaque is relatively liquid with a large amount of fat and relatively little supporting collagen. Application of a high intensity laser beam causes the collagen within the plaque to cross link with other collagen such that the plaque is solidified and made less dangerous. This coagulates the protein in the plaque. When the laser 42 is on, the laser 38 would normally be off, and vice versa.

When the applied laser energy 46 from distal end 14 strikes tissue 16 and stimulates fluorescence, the fluorescent light 48 enters the distal end of fiber 24 through a lens arrangement 25, (such as those detailed in the incorporated by reference '265 and '743 patents). Importantly, the use of the saline or other flushing solution highly transparent to the laser energy and the fluorescent light wavelengths allows for highly efficient collection of the fluorescent light. The double hood arrangement provides a continuous stream of saline out of opening 26. This provides a relatively clear path for laser beam 46 and minimizes any interference from blood which might otherwise dissipate the fluorescent light before it is collected in fiber 24.

This fluorescent light passes along fiber 24 into port 32B and out of port 32C to fiber 50 and into diode detector 52. Detector 52 supplies an electrical signal to fluorescence detector 54 based on the optical signal supplied to detector 52. Fluorescence detector 54 processes the electrical signal supplied to it and, in turn, supplies an electrical signal to an optical multichannel analyzer (OMA) 56. Components 52 and 54 are often combined as a single device. Fluorescence detector 54 can also be called a polychrometer.

The detection arrangement of components 52, 54, and 56 could be replaced by other detection arrangements. Preferably, a highly sensitive detector capable of sensing single photons would be used. In any case, the detector arrangement or subsystem that is used would allow detection of tissue characteristics corresponding to dangerous plaque (i.e., plaque prone to rupture or thrombosis). For example, the OMA 56 can provide data to compile an amplitude versus wavelength graph such as 58. The characteristics of the graph such as the wavelength of the peak allow one evaluate the danger from plaque on tissue 16. The amplitude, steepness, and spectral location of peaks in the fluorescence (i.e., wavelengths of greatest amount of light) are indicative of the characteristics of the plaque including the thickness of its collagen which supports the fat in the plaque. Insufficiently thick collagen is generally more dangerous for a given amount of fat. The collagen exhibits fluorescence at a given wavelength and a steep high amplitude peak at that wavelength is indicative of a large amount of collagen. If desired, the data corresponding to the graph could be processed by a computer (not separately shown, but would be at box 58), which could evaluate the plaque danger using signal processing software on the data generated by the tissue's fluorescence.

Note that the distal end 14 of catheter 12 is moved lengthwise to determine plaque characteristics at different linear points in an artery. Additionally, the distal end can be rotated to determine characteristics at different angular positions in the circumference of the artery. If desired, a catheter arrangement having an inner catheter rotatable relative to an outer catheter as disclosed in U.S. Pat. Nos. 5,651,785 and 5,464,404 issued respectively on Jul. 29, 1997 and Sep. 20, 1993 could be used in realizing the present invention. This can be used to create a topical map of plaque area characteristics relative to vulnerability to rupture and thrombos. The map would show danger based on linear and angular position of the plaque. Those patents, which name the present inventor as a co-inventor, are hereby incorporated by reference.

Figure 2:
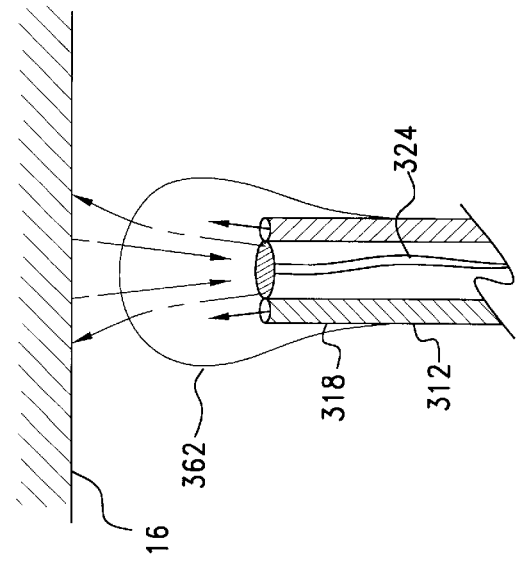
FIG. 2 is a simplified side view with portions in cross section of a distal end of a second embodiment catheter.

Turning now to FIG. 2, an alternate embodiment for the distal end of the catheter is shown. The components and operations at the proximal end would be as discussed for FIG. 1. The parts in the FIG. 2 embodiment are labeled in the "100" series with the same last two digits as the corresponding part, if any, of the FIG. 1 embodiment. Thus, catheter 112 has outer hood 118, inner hood 120, flushing solution channel 122, optical fiber 124, and opening 126 constructed and operable the same as their corresponding FIG. 1 parts except as noted hereafter. A clear latex balloon 160 is on the side of the distal end of the catheter 112. When the distal end 118 is in proper position, the pressure of saline in channel 122 is increased causing inflation of the balloon 160. The balloon 160 can be inflated with the clear saline such that longer periods (i.e., longer than for the FIG. 1 arrangement) of blood displacement for the laser and fluorescent light passage can be maintained. The balloon is sufficiently clear that the laser and fluorescent light readily passes through it. The balloon can be inflated to extend completely from the distal end 114 to the tissue 16, although it is not inflated that much in the view of FIG. 2.

Figure 3:
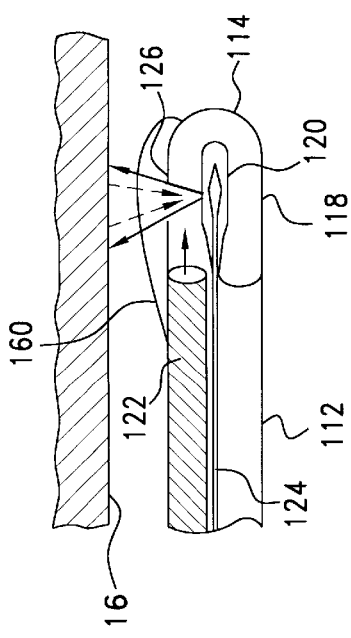
FIG. 3 is a simplified side view with portions in cross section of a distal end of a third embodiment catheter.

Turning now to FIG. 3, an alternate embodiment for the distal end of the catheter is shown. The components and operations at the proximal end would be as discussed for FIG. 1. The parts in the FIG. 3 embodiment are labeled in the "200" series with the same last two digits as the corresponding part, if any, of the FIG. 1 embodiment. Thus, catheter 212 has outer hood 218, inner hood 220, flushing solution channel 222, optical fiber 224, and opening 226 constructed and operable the same as their corresponding FIG. 1 parts except as noted hereafter. Catheter 212 is an end firing arrangement where the opening 226 is at the tip of distal end 214, instead of the side wall.

Depending on the location of the plaque either the side firing technique (laser exits catheter from the side as in FIGS. 1 and 2) or the end firing technique of FIG. 3 may be used.

Figure 4:
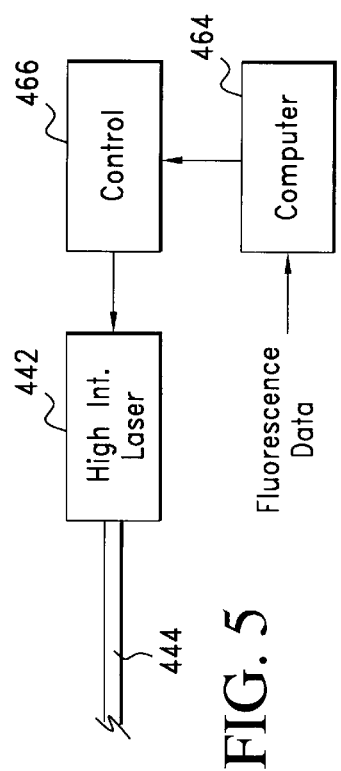
FIG. 4 is a simplified side view with portions in cross section of a distal end of a fourth embodiment catheter.

FIG. 4 is an embodiment with parts labeled in the "300" series with the same last two digits as the corresponding part, if any, of the FIG. 1 embodiment. Catheter 312 is shown simplified with just components 318 and optical fiber 324 labeled. Catheter 312 is an end firing arrangement with a clear latex balloon 362 on the distal end of the catheter 312.

Figure 5:
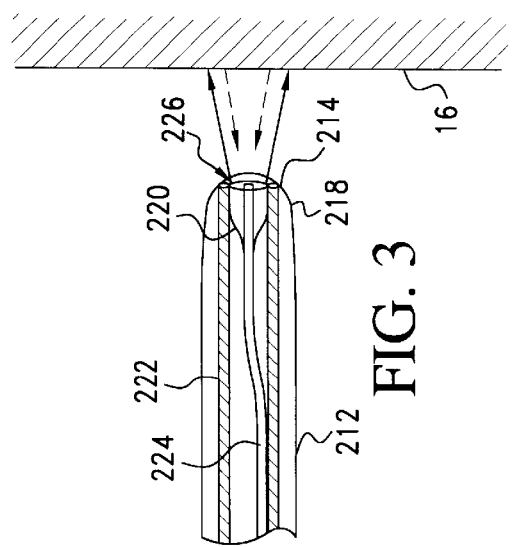
FIG. 5 is a block diagram of a feedback arrangement according to one aspect of the present invention.

FIG. 5 shows a simplified block diagram of an additional feature which could be used as a modification of some of the proximal portions of system 10 of FIG. 1. The high intensity laser 442 and fiber 444 respectively would be used in place of laser 42 and fiber 44 in FIG. 1. The fluorescence data (i.e., from OMA 56 in FIG. 1) is supplied to a computer 464 which performs signal processing. The arrangement of FIG. 5 may provide several alternate control features.

A first control feature that FIG. 5 may provide involves alternately firing the high intensity laser 442 and the low intensity laser (such as 38 of FIG. 1). After the low intensity laser senses dangerous plaque, the high intensity laser heats and solidifies the plaque for a period of time. The high intensity laser turns off and the low intensity laser turns on. The computer 464 then detects the fluorescence from the treated tissue. If more treatment or solidification of the plaque is appropriate, the computer signals control 466 which turns on laser 442 for a second application of high intensity laser energy to the tissue. (The control 466 may also turn on and off the low intensity laser 38.) For a given portion of arterial wall tissue, alternate sensing tissue characteristics and changing them (i.e., solidifying plaque by application of high energy laser beam) can be performed until the tissue characteristics have been changed sufficiently to reduce the danger from the plaque.

A second control technique possible with FIG. 5 senses the fluorescence from the tissue under the high intensity laser energy. Depending on the wavelength of the high intensity laser, this fluorescence may differ in distribution from that produced by the low intensity laser. However, it may advantageously be used to indicate the tissue characteristics in realtime as the high intensity laser is treating the plaque. When the plaque is sufficiently solidified, the computer signals control 466 to turn off the high intensity laser.

A third control strategy works like the second control strategy except that the low intensity laser is left on such that fluorescence data from the tissue responding to the low intensity laser is continuously received even as the high intensity laser is on. In other words, after the low intensity laser has helped detect an area requiring treatment, both lasers are turned on such that treatment and sensing take place simultaneously. This technique would use filtering of the optical signals, electrical signals, or simply computer filtering of the data to minimize any contribution of the high intensity laser to the fluorescence of the tissue. Alternately, the signal processing of computer 464 would take the tissue characteristics from fluorescence stimulated by both of the lasers.

Although the discussion herein of the optional treatment of detected dangerous plaque has concentrated on the use of high intensity laser energy, one could alternately treat the dangerous plaque by use of radio frequency (RF) energy to heat the plaque and solidify it. Electrical resistance heating or other heating techniques could alternately be used. Further, chemical agents applied to the plaque to solidify it could by used instead of heating. For example, the flush solution channel 22 could provide alcohol to solidify plaque after detection of dangerous plaque.

The discussion herein has concentrated on the detection of dangerous plaque in arteries. However, the present techniques of providing clear paths for laser energy and resulting fluorescence by release of clear solution (FIGS. 1 and 3) and providing clear paths for laser energy and resulting fluorescence by catheter balloons with clear solution (FIGS. 2 and 4), could also be used for sensing heart tissue characteristics, sensing tissue characteristics in the esophagus, or sensing characteristics (presence of tumors or other properties) of other tissues.

Although specific constructions have been presented herein, it is to be understood that these are for illustrative purposes only. Various modifications and adaptations will be apparent to those of skill in the art. In view of possible modifications, it will be appreciated that the scope of the present invention should be determined by reference to the claims appended hereto.

What is claimed is:

1. A system for medical diagnosis comprising:
    a catheter with a proximal end and a distal end and having:
        an outer hood having a first opening disposed therein;
        an optical fiber having a tip within the outer hood, the optical fiber operable to output a diagnostic laser beam with a central axis extending from the tip through the first opening;
        a lens at the tip of the optical fiber; and
        a channel connected to the outer hood and extending along the catheter for supplying flushing solution to within the outer hood such that the flushing solution flows out of the first opening; and
        a detection subsystem operably connected to the proximal end of the catheter and operable to detect fluorescent light from tissue illuminated by the diagnostic laser beam, the fluorescent light having passed through the lens and from the distal end of the catheter to the proximal end of the catheter along the optical fiber, the optical fiber thus passing the diagnostic laser beam out of its tip and through the lens after passing in one direction in the optical fiber and receiving the fluorescent light into the tip of the optical fiber and passing along the optical fiber in a direction opposite to said one direction.

2. The system of claim 1 further comprising an inner hood within the outer hood, the tip being disposed within an interior of the inner hood.

3. The system of claim 1 further comprising a diagnostic laser operably connected to the proximal end of the catheter and applying energy to the optical fiber such that the optical fiber outputs the diagnostic laser beam at the distal end.

4. The system of claim 3 further comprising a coupler operably connected to carry laser energy from the diagnostic laser to the optical fiber and to carry fluorescent light from the optical fiber to the detection subsystem.

5. The system of claim 4 wherein the detection subsystem detects tissue characteristics by detecting fluorescence peaks.

6. The system of claim 5 further comprising a balloon attached at the distal end of the catheter and operable to inflate upon pressure from solution in the channel, the balloon providing a clear path for laser energy and fluorescent light between the tip and the illuminated tissue.

7. The system of claim 1 wherein the detection subsystem detects tissue characteristics by detecting fluorescence peaks.

8. The system of claim 1 further comprising a balloon attached at the distal end of the catheter and operable to inflate upon pressure from solution in the channel, the balloon providing a clear path for laser energy and fluorescent light between the tip and the illuminated tissue.

9. The system of claim 1 wherein the catheter is operable to provide treatment to tissue upon the system detecting appropriate locations for treatment.

10. The system of claim 9 further comprising a treatment laser operably connected to the proximal end to supply treatment laser energy for passage along the optical fiber and out of the tip.

11. The system of claim 1 wherein the optical fiber is the only optical fiber in the catheter.

12. A method of medical diagnosis, the steps comprising:
    inserting a distal end of a catheter into a patient, the catheter also having a proximal end and including an outer hood having a first opening disposed therein, an inner hood within the outer hood, an optical fiber having a tip within an interior of the inner hood and a lens at the tip;
    outputting a diagnostic laser beam from the optical fiber, through the lens within the outer hood to pass through the opening and be applied to tissue of the patient;
    sensing fluorescent light passing through the lens from the laser stimulation of the tissue; and
    supplying clear solution to the opening such that the diagnostic laser beam and the fluorescent light have relatively clear paths; and wherein the fluorescent light that is sensed passes through the opening along the relatively clear path established by the supplying of clear solution.

13. The method of claim 12 wherein the catheter includes an optical fiber extending from the distal end to the proximal end and the step of outputting the diagnostic laser beam from within the outer hood results from application of laser energy to the proximal end of the optical fiber.

14. The method of claim 13 wherein the sensing of fluorescent light from the laser stimulation of the tissue is accomplished by having fluorescent light pass along the optical fiber from the distal end to the proximal end and enter a detection subsystem at the proximal end.

15. The method of claim 14 wherein the detection subsystem detects tissue characteristics by detecting fluorescence peaks.

16. The method of claim 15 wherein the detection subsystem detects plaque that is prone to rupture or thrombosis.

17. The method of claim 12 further comprising detecting tissue characteristics by detecting fluorescence peaks.

18. The method of claim 17 wherein the detected tissue characteristics correspond to plaque that is prone to rupture or thrombosis.

19. The method of claim 12 wherein the tissue is an arterial wall being tested for plaque.

20. The system of claim 12 further comprising inflating a balloon attached at the distal end of the catheter by pressure from solution in the channel, the balloon providing a clear path for laser energy and fluorescent light between the tip and the illuminated tissue.

21. The method of claim 12 wherein the catheter used in the inserting step includes only one optical fiber.

22. A method of medical diagnosis, the steps comprising:
    inserting a distal end of a catheter into a patient, the catheter also having a proximal end;
    outputting a diagnostic laser beam from a lens at the distal end of the catheter and applying the diagnostic laser beam to tissue of the patient;
    sensing fluorescent light from the laser stimulation of the tissue; and
    wherein the catheter includes an optical fiber extending from the distal end to the proximal end and the step of outputting the diagnostic laser beam results from application of laser energy to the proximal end of the optical fiber; and wherein the sensing of fluorescent light from the laser stimulation of the tissue is accomplished by having fluorescent light pass along the optical fiber from the distal end to the proximal end, after passage through the lens at the distal end, and enter a detection subsystem at the proximal end, the optical fiber thus passing fluorescent light in one direction and passing laser energy for the diagnostic laser beam in a direction opposite to said one direction.

23. The system of claim 22 wherein the optical fiber is the only optical fiber in the catheter.

* * * * *